United States Patent [19]

Johnston et al.

[11] Patent Number: 4,891,591

[45] Date of Patent: Jan. 2, 1990

[54] NONINTRUSIVE METHOD AND APPARATUS FOR MONITORING THE CURE OF POLYMERIC MATERIALS

[75] Inventors: David F. Johnston, Hampton; Robert L. Fox, Hayes, both of Va.

[73] Assignee: The United States of America as represented by the Administrator of the National Aeronautics and Space Administration, Washington, D.C.

[21] Appl. No.: 133,413

[22] Filed: Feb. 16, 1988

[51] Int. Cl.$^4$ .................... G01N 27/72; G01R 33/12; G01R 27/00

[52] U.S. Cl. .................................. 324/234; 264/40.1; 324/236; 526/60

[58] Field of Search ................ 324/204, 224, 234, 236, 324/65 R, 65 P, 229, 233; 526/59, 60; 264/40.1

[56] References Cited

U.S. PATENT DOCUMENTS

| | | | |
|---|---|---|---|
| 2,587,631 | 3/1952 | Kuehne | 324/229 |
| 2,772,393 | 11/1956 | Davis | 324/236 X |
| 2,859,407 | 11/1958 | Henisch | 324/234 X |
| 3,152,303 | 10/1964 | Lary . | |
| 3,234,461 | 2/1966 | Trent et al. | 324/234 X |
| 3,234,462 | 2/1966 | Holdsworth . | |
| 3,248,925 | 5/1966 | Warfield | 324/71.4 X |
| 3,255,405 | 7/1966 | French | 324/234 |
| 3,358,225 | 12/1967 | Peugeot | 324/234 X |
| 3,444,460 | 5/1969 | Penney | 324/236 X |
| 3,473,111 | 10/1969 | Leersnijder et al. | 324/236 |
| 3,477,018 | 11/1969 | Richardson et al. | 324/236 X |
| 3,586,966 | 6/1971 | Haisty et al. | 324/236 |
| 3,791,792 | 2/1974 | Lindsay . | |
| 3,936,734 | 2/1976 | Brandli . | |
| 4,007,319 | 2/1977 | Weisser et al. | 526/60 |
| 4,105,971 | 8/1978 | Nevalainen | 324/224 X |
| 4,207,519 | 6/1980 | Zatsepin | 324/235 |
| 4,763,071 | 8/1988 | McGee et al. | 324/233 |

Primary Examiner—Gerard R. Strecker
Attorney, Agent, or Firm—Harold W. Adams; John R. Manning; Charles E. B. Glenn

[57] ABSTRACT

The invention is a nonintrusive method of monitoring the cure of a polymeric material using an electromagnetic field to sense a change of resistance of the polymeric material in the electromagnetic field that occurs during curing. This change of resistance is used to vary the impedance of an alternating voltage power supply that produces the electromagnetic field and which change of impedance is measured periodically or continuously to monitor the cure of said polymeric material.

Apparatus for practicing the method of this invention may include a nonintrusive sensing head 11 providing an inner, electromagnetic core 12 within an open ended outer pot 14 formed of magnet material, the open end 17 of the pot core 14 being positioned from a selected area of the surface of a sheet 27 of the polymeric material. An alternating voltage supply circuit that includes an inductance coil 18 around said electromagnetic core 12 and a capacitor 23 connected in parallel with said inductance coil 18 to form a resonant tank circuit when energized. The resulting change in resistance of the polymeric material opposite said open end 17, a function of the curing thereof, is measured as a corresponding change in the impedance of said power supply circuit to thereby monitor the cure of the polymeric material in the selected area.

10 Claims, 3 Drawing Sheets

NONINTRUSIVE METHOD AND APPARATUS FOR MONITORING THE CURE OF POLYMERIC MATERIALS

ORIGIN OF THE INVENTION

The invention described herein was made by employees of the United States Government and may be manufactured and used by or for the Government for governmental purposes without the payment of any royalties thereon or therefor.

BACKGROUND OF THE INVENTION

1. Field of the Invention

The invention relates to a nonintrusive method and apparatus for monitoring the cure of thermosetting polymeric materials.

2. Description of Prior Art

Methods of and apparatus for monitoring the curing of thermosetting polymeric materials using capacitive gauges are generally known. Thermosetting polymers the resistance of which varies during curing include composites formed of several layers of woven graphite fibers impregnated with a thermosetting matrix of an epoxy.

A disadvantage in using capacitive gauges to monitor the curing of thermosetting composites as is conventional is that leads from the gauge must be inserted into the composite material leaving voids in the material when removed after curing is completed. In the case of laminated composite thermosetting materials, leads from the capacitive gauge may need to be mounted permanently between layers to monitor the curing process.

SUMMARY OF THE INVENTION

An object of this invention is to provide nonintrusive methods and apparatus for monitoring the cure of polymeric materials such as composites formed of layers of graphite fibers impregnated with a thermosetting matrix of a polymeric material that senses the change of resistance of the polymeric material during the curing process.

Another object of the invention is to provide such methods and apparatus in which changes in the resistance of polymeric materials while curing are used to change the impedance of a series electrical circuit.

The above and numerous other objects may be achieved by the invention which includes a nonintrusive sensing head providing an inner electromagnetic core within an open ended outer pot of magnetic material, the open end of the outer core being positioned from a sheet of polymeric material at a constant distance either periodically or continuously during a curing process. The inner electromagnetic core is energized by an alternating voltage supply circuit that includes an inductance coil around said electromagnetic core and a capacitor connected parallel thereto, said inductance coil and said capacitor forming a tuned circuit resonant with the frequency of said alternating voltage supply when energized at which time changes in the resistance of said polymeric material during curing and which are a function thereof are monitored by sensing the resulting change of impedance of said tuned circuit.

In an alternative method and apparatus, the resistance of the polymeric material changes during curing, to change the impedance of a series circuit including an inductance coil around an electromagnetic sensor core measuring the resulting change of phase of the alternating supply voltage monitors the curing of the polymeric material.

BRIEF DESCRIPTION OF THE DRAWINGS

Numerous other objects and advantages of the invention will become apparent from the following description when read in view of the appended drawings, wherein.

DESCRIPTION OF PREFERRED EMBODIMENTS OF THE INVENTION

Figure 1:
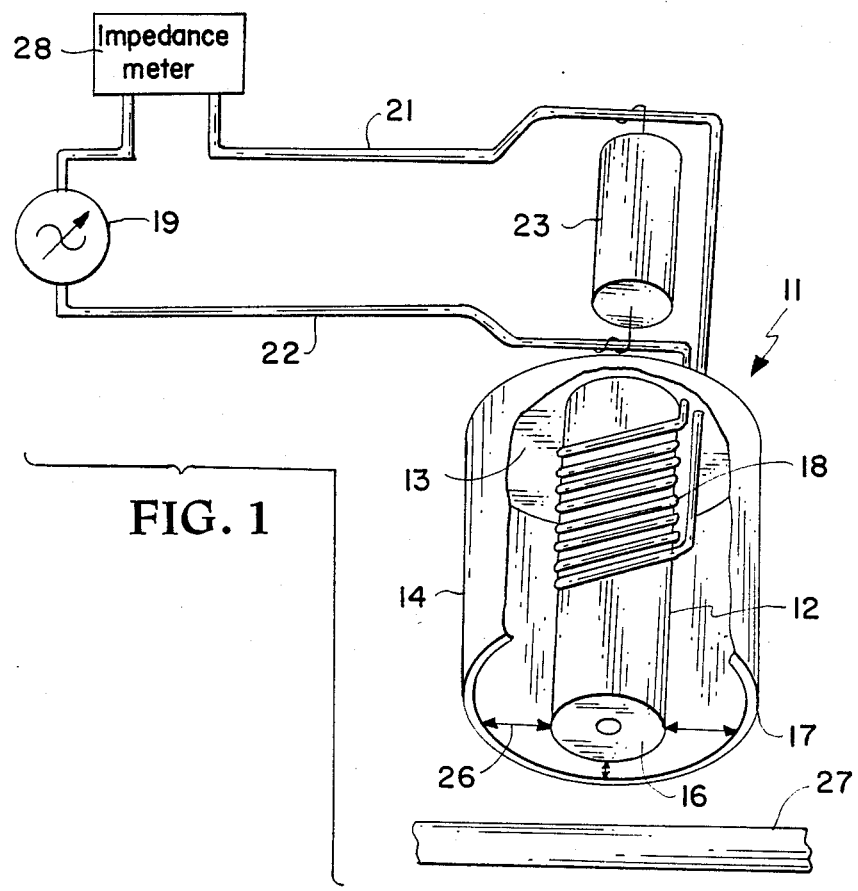
FIG. 1 is a perspective, partial sectional view of a preferred embodiment of the apparatus for practicing the method of this invention using a nonintrusive sensing head.

Referring to the drawings, FIGS. 1–5 illustrate a preferred embodiment of the apparatus for practicing the method of the invention as including a nonintrusive sensing head generally designated by the reference numeral 11 which includes an inner, cylindrical core 12 formed of an electromagnetic material such as bonded powder irons having a relatively low Curie temperature of about 400° F. The choice of material used for the inner, electromagnetic core is determined by the curing temperature to which the sensing head 11 is exposed during use.

The inner core 12 is attached to the base 13 of an open ended and surrounding outer, cylindrical pot core 14 of the same magnetic material as the inner core 12, the inner core 12 extending along the longitudinal axis of the outer pot core 14, its flat, circular end face 16 lying in the circular plane of the open end 17 of the pot core 14.

An inductor coil 18 around the inner core 12 is connected in series to a suitable alternating current voltage power supply 19 by means of leads 21 and 22, the number of turns in the coil 18 determining its inductance. A capacitor 23 is connected across the leads 21 and 22 in parallel with the inductor coil 18, the respective circuit reactance values of the inductor coil 18 and capacitor 23 being selected to provide a substantially tuned, resonant circuit when energized with the AC voltage power supply 19 of a given frequency.

Figure 2:
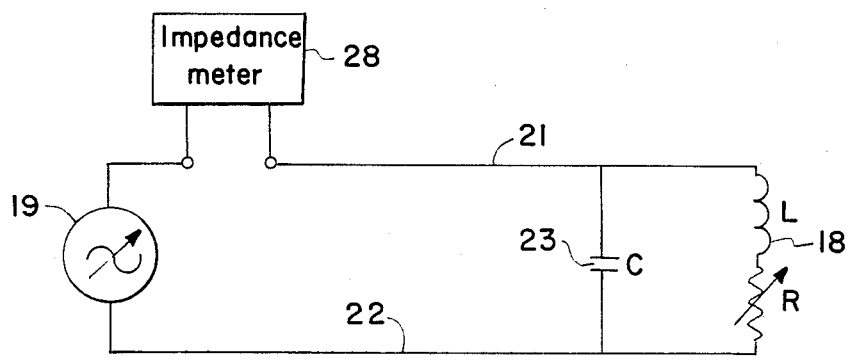
FIG. 2 is a schematic of the equivalent electrical circuit of the nonintrusive sensing head when used to monitor the cure of a sheet of polymeric material.
Figure 3:
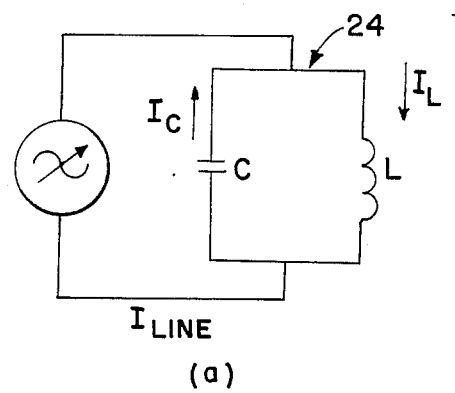
FIG. 3 including portions (a)–(c) schematically illustrates the equivalent electrical circuit of an ideal tank tuned circuit.
Figure 3:
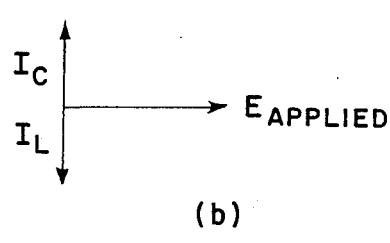

Resonance in this circuit occurs when the reactance of the respective inductor coil 18 and capacitor 23 are equal, the remaining circuit impedance being primarily a variable resistance R which is substantially in series with the inductor coil 18 as shown in FIG. 2.

FIG. 3(a)–(c) schematically illustrate an ideal, parallel tank circuit 24 at resonance as having zero line current although equal currents $I_L$ and $I_c$ of opposite phase flow in the parallel inductor coil L and capacitor C, respectively. The quality factor of this tank circuit is referred to as Q which is determined as shown in FIG.

3(c). As ideal tank circuits for this type of application are not presently available, a variable frequency, low voltage is used to energize the tuned circuit of the sensing head 11.

Figure 4:
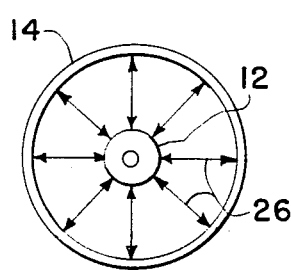
FIG. 4 is an end view of the nonintrusive sensing head shown in FIG. 1.

FIG. 4 illustrates the lines of flux 26 within the resulting magnetic field between the inner core 12 and outer pot core 14 when the sensing head is energized. When the sensing head 11 is positioned at a constant distance over a sheet 27 of polymeric material with the end face 16 of the inner core 12 substantially parallel thereto, the magnetic field which is directed into that part of the material under the head induces an electromotive force or voltage (Back EMF) that generates an eddy current that varies with changes in the resistance R of the polymeric material subjected to the electromagnetic field.

This changes the conductive path between the inner core 12 and outer pot core 14, the changing resistance R effectively appearing in series with the inductor coil 18 as shown in FIG. 2. Thus changes in R due to curing of the material are sensed by the electromagnetic field causing changes in the impedance of the resonant tank circuit formed by the inductor coil 18 and capacitor 23. These changes in the impedance of the resonant tank circuit may be measured by a suitable test meter 28, such as a vector impedance analyzer, Model HP 4192A made by Hewlett Packard Company, 1820 Embarcardero Road, Palo Alto, California 94303-9957, either periodically or continuously thus monitoring the cure of the polymeric material.

The test meter 28 measures the change in impedance of the supply circuit which is essentially the change in the variable resistance R. This in turn varies the Q of the resonant tank circuit which may also be measured to monitor the cure of the polymeric sheet.

Nonintrusive monitoring of the sheet 27 of polymeric material to be cured may be practiced internally or externally of the oven or chamber in which curing is to take place. It is important that the Curie point of the electromagnetic material used to form the inner core 12 and outer pot core 14 be lower than the curing temperature with which used.

When extremely high curing temperatures are used, the capacitor 23 may be mounted externally of the curing oven. In practice, the distance between the end face 16 of the inner core 12 is constant and the face preferably positioned parallel with the surface of the polymeric sheet. This fixed distance may be varied when the sensing head 11 is used to monitor the curing of different types, shapes and thicknesses of polymeric materials.

After first measuring the resistance R of the sheet 27 of polymeric material, curing may thereafter be nonintrusively monitored by this method, either continuously or periodically by positioning the sensing head 11 within a curing oven and selectively moving the sensing head over the surface of a stationary sheet 27 of polymeric material to be cured in the oven as previously described. As any change of resistance R in the polymeric sheet directly under the outer core 14 is measured substantially instantaneously, monitoring may be continuous or at selected surface areas where the sensing head 11 is periodically positioned.

Figure 5:
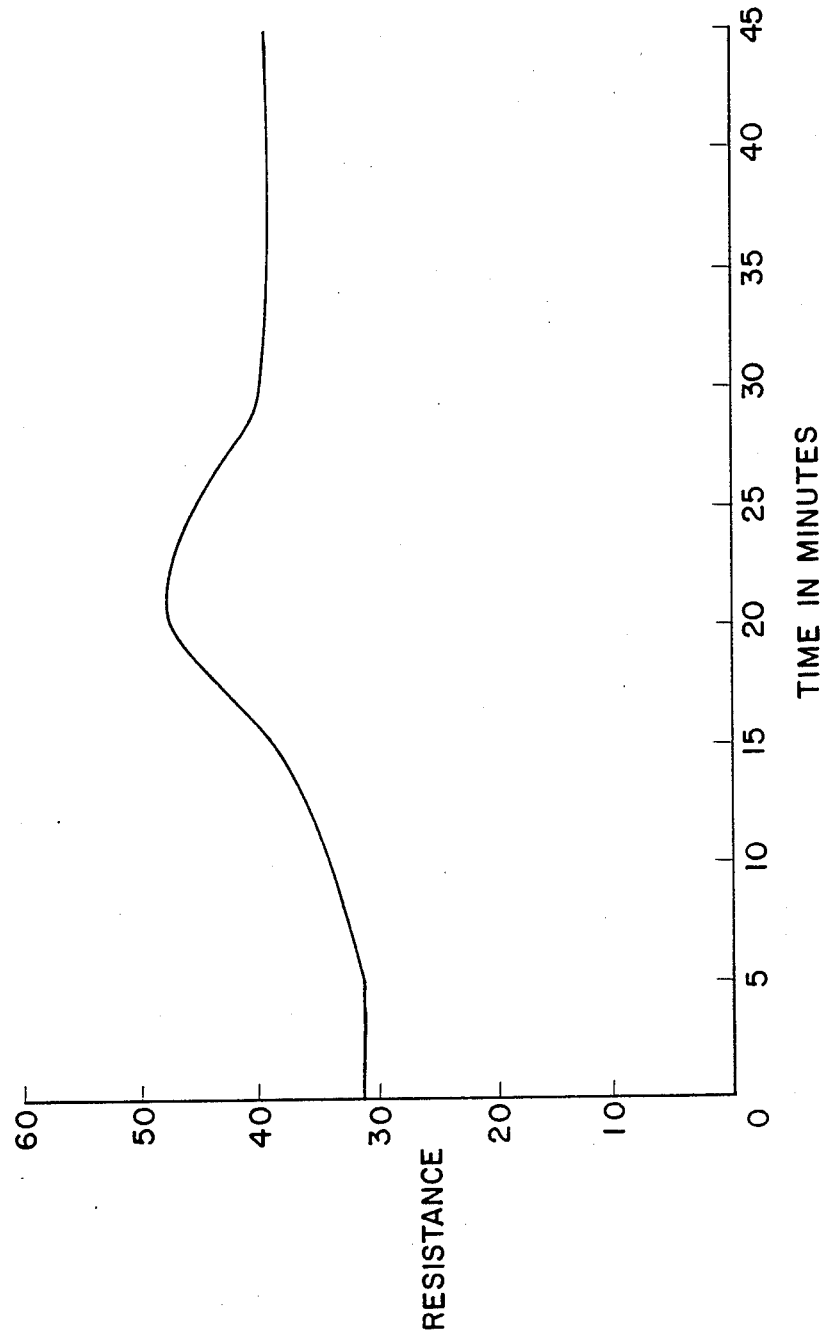
FIG. 5 is a graph illustrating the change of resistance of a typical polymeric material during curing.

The sheet 27 of polymeric material may also be moved relative to a stationary sensing head 11 to achieve the same results. As shown in FIG. 5, the variable resistance R of the sheet 27 reaches a peak value during curing and thereafter decreases to a substantially constant value indicating the curing process has been completed at which point it may be terminated.

An alternative method of practicing the invention is to periodically remove the sheet 27 of polymeric material from the oven during the curing cycle and measuring any change of resistivity of the sheet at the same surface area where previously measured. As in the internal oven monitoring method, the sheet 27 may be moved relative to the sensing head 11 or vice versa. The resulting measurements of the impedance of the L-C tank circuit may be recorded or visually displayed substantially as shown in FIG. 5.

DESCRIPTION OF ALTERNATIVE EMBODIMENTS OF THE INVENTION

Figure 6:
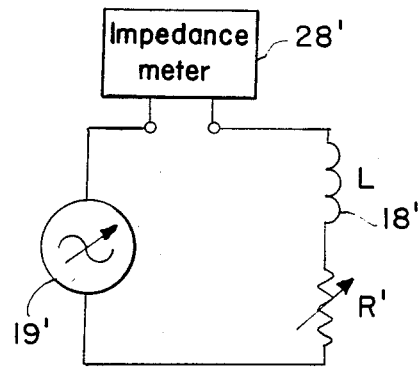
FIG. 6 is an electrical schematic of an alternative embodient of the nonintrusive sensing head.

An alternative method of an apparatus for nonintrusively monitoring the curing of a polymeric material is provided by removing the capacitor 23 as shown in FIG. 6. In this arrangement, the change of resistance of the polymeric material during curing as previously described effectively appears as a variable resistor R' connected in series with an inductor coil 18' in the AC voltage supply circuit 19'.

Changes in the value of resistor R' varies the impedance of the AC voltage supply circuit which may be directly measured using suitable measurement means such as a voltage phase meter 28' to effectively monitor the curing process. As will be apparent, the alternative embodiment of the apparatus may be used to nonintrusively monitor the curing of a polymeric material either internally or externally of a curing oven as previously described.

While preferred embodiments have been described in detail, numerous changes and modifications may be made within the principles of the inventions which are to be limited only by the appended claims.

We claim:

1. A nonintrusive method of monitoring the cure of a sheet of polymeric material the resistance R of which varies from an uncured value to a cured value during curing comprising the steps of:

determining the initial value of the resistance R of an uncured sheet of polymeric material;

subjecting said uncured sheet of polymeric material to a curing temperature;

subjecting one or more selected portions of said sheet of polymeric material to an electromagnetic field from an electromagnet supported a determined distance from said sheet of polymeric material and established by an alternating voltage supply circuit connected to said electromagnet;

sensing the variation in resistance R in said one or more selected portions of said polymeric material with said magnetic field, said variation in resistance R from said uncured to said cured value changing the impedance of said supply circuit; and measuring the change in impedance of said supply circuit to monitor the cure of said sheet of polymeric material in said one or more selected portions thereof.

2. The method of claim 1 wherein the variation of said resistance R in said one or more selected portions of said sheet of polymeric material is sensed periodically.

3. The method of claim 1 wherein the variation in said resistance R in said one or more selected portions of said polymeric material is sensed continuously.

4. The method of claim 1 wherein said sheet of polymeric material is periodically removed from said curing temperature.

5. In an apparatus for monitoring the cure of a sheet of polymeric material the resistance R of which varies from an uncured to a cured value during curing the improvement comprising;
   an electromagnetic sensing head including an inductor coil for passing a magnetic field through one or more selected portions of said sheet of polymeric material when said inductor coil is energized;
   a series connected alternating voltage supply circuit for energizing said inductor coil, said electromagnetic sensing head sensing the variation in resistance R from said uncured to said cured value in said one or more selected portions of said sheet of polymeric material and changing the impedance of said series connected supply circuit; and
   means for measuring said changes in said impedance of said supply circuit to non-intrusively monitor the cure of said sheet of polymeric material in said one or more selected portions thereof.

6. The invention as defined in claim 5 including a capacitor connected in parallel with said inductor coil, said capacitor and said inductor coil forming a resonant tank circuit during said curing.

7. The invention as defined in claim 5 wherein said sensing head includes an inner cylindrical core of magnetic material having a substantially flat end face and an outer cylindrical and open ended surrounding pot core of magnetic material spaced from and attached to said inner core.

8. The invention as defined in claim 7 wherein said flat end face of said inner cylindrical core and the open end of said outer pot core are in the same plane which extends substantially parallel to the surface of said sheet of polymeric material.

9. The method of claim 1 wherein said cured value of said resistance R becomes substantially constant during curing.

10. The method of claim 9 wherein said resistance R increases from said uncured value to a peak value before decreasing to said substantially constant cured value.

* * * * *